US00PP28650P2

(12) United States Plant Patent
Hartman

(10) Patent No.: US PP28,650 P2
(45) Date of Patent: Nov. 14, 2017

(54) ***CALADIUM* PLANT NAMED 'BERRIES N' BURGUNDY'**

(50) Latin Name: *Caladium×hortulanum*
Varietal Denomination: Berries N' Burgundy

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 36 days.

(21) Appl. No.: 14/999,321

(22) Filed: Apr. 25, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — C. A. Whealy

(57) ABSTRACT

A new and distinct cultivar of *Caladium* plant named 'Berries N' Burgundy', characterized by its short height; somewhat mounded plant habit; moderately vigorous growth habit; moderate growth rate; fancy-type leaves that are dark green in color overlain with a variable reddish bronze cast; and pink-colored petioles with brown-colored stripes.

4 Drawing Sheets

Botanical designation: *Caladium×hortulanum.*
Cultivar denomination: 'BERRIES N' BURGUNDY'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Berries N' Burgundy'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2009 in Avon Park, Fla. of *Caladium×hortulanum* 'White Dynasty', disclosed in U.S. Plant Pat. No. 22,240, as the female, or seed, parent with *Caladium×hortulanum* 'Blaze', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2010.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2011 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Berries N' Burgundy'. These characteristics in combination distinguish 'Berries N' Burgundy' as a new and distinct *Caladium* plant:

1. Short in height, and somewhat mounded plant habit; leaf petioles upright to outwardly arching with development.
2. Moderately vigorous growth habit and moderate growth rate.
3. Fancy-type leaves that are dark green in color overlain with a variable reddish bronze cast; areas surrounding the midvein and lateral veins are variably suffused with grey green-colored flecks with red orange to coral pink-colored veins.
4. Petioles that are pink in color with brown-colored stripes.

Plants of the new *Caladium* differ primarily from plants of the female parent, 'White Dynasty', in the following characteristics:

1. Plants of the new *Caladium* are shorter than plants of 'White Dynasty'.
2. Plants of the new *Caladium* have fancy type leaves whereas plants of 'White Dynasty' have strap (or lance) type leaves.
3. Plants of the new *Caladium* and 'White Dynasty' differ in leaf color as leaves of 'White Dynasty' are white and greyed green in color with few random red purple-colored spots, dark green-colored margins and greyed green- colored venation.
4. Plants of the new *Caladium* and 'White Dynasty' differ in leaf petiole color as leaf petioles of 'White Dynasty' are green in color, tinged and streaked with brown.

Plants of the new *Caladium* differ primarily from plants of the male parent, 'Blaze', in the following characteristics:

1. Plants of the new *Caladium* are more shorter than plants of 'Blaze'.
2. Plants of the new *Caladium* and 'Blaze' differ in leaf color as leaves of 'Blaze' are dark green in color with burgundy red-colored venation and centers.

Plants of the new *Caladium* can be compared to plants of *Caladium×hortulanum* 'John Peed', not patented. In side-by-side comparisons, plants of the new *Caladium* differ primarily from plants of 'John Peed' in the following characteristics:

1. Plants of the new *Caladium* are shorter than plants of 'John Peed'.
2. Plants of the new *Caladium* and 'John Peed' differ in leaf color as leaves of 'John Peed' have dark red-colored centers and red-colored venation with olive green-colored margins.

Plants of the new *Caladium* can be compared to plants of *Caladium×hortulanum* 'Frieda Hemple', not patented. In side-by-side comparisons, plants of the new *Caladium* differ primarily from plants of 'Frieda Hemple' in the following characteristics:

1. Plants of the new *Caladium* are shorter than plants of 'Frieda Hemple'.
2. Plants of the new *Caladium* and 'Frieda Hemple' differ in leaf color as leaves of plants of 'Frieda Hemple' are medium green in color with bright red-colored centers and venation.
3. Plants of the new *Caladium* and 'Frieda Hemple' differ in leaf petiole color as leaf petioles of 'Frieda Hemple' are tan pink in color with dense blackish brown stippling and streaks, appearing to be close to black in color.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Berries N' Burgundy' in a container and grown in a shadehouse (tuber de-eyed).

The photograph at the top of the second sheet is a comparison view of typical potted plants of the male parent, 'Blaze' (left), 'Berries N' Burgundy' (center) and the female parent, 'White Dynasty' (right).

The photograph at the bottom of the second sheet is a comparison view of typical potted plants of 'John Peed' (left), 'Berries N' Burgundy' (center) and 'Frieda Hemple' (right).

The photograph at the top of the third sheet is a comparison view of typical plants of 'Berries N' Burgundy' grown in containers; the plant on the left has not had its tuber de-eyed and the plant on the right has had its tuber de-eyed prior to planting.

The photograph at the bottom of the third sheet is a side perspective view of typical plants of 'Berries N' Burgundy' grown in an open field.

The photograph at the top of the fourth sheet is a close-up view of typical freshly-harvested tubers with roots of 'Berries N' Burgundy'.

The photograph at the bottom of the fourth sheet is a close-up view of a typical inflorescence of 'Berries N' Burgundy'.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were ten weeks old and plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Berries N' Burgundy'.

Parentage:

*Female, or seed, parent.*—*Caladium×hortulanum* 'White Dynasty', disclosed in U.S. Plant Pat. No. 22,240.

*Male, or pollen, parent.*—*Caladium×hortulanum* 'Blaze', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented; individual segments ovate to somewhat irregular in shape. Height: About 3.6 cm. Diameter: About 4.5 cm to 7.1 cm. Segment height: About 2.2 cm. Segment diameter: About 2.2 cm to 3.2 cm. Axillary buds, height: About 9 mm. Texture: Thick, starchy; somewhat brittle. Color: Epidermis, freshly-harvested: Close to 159B variably tinged with close to 179B to 179C; outer skin, close to 199B. Epidermis, dried: Close to 200A. Cortical tissue: Close to 2D. Axillary buds: Close to 27D. Root description: Thick, fleshy contractile roots; color, close to 155C to 155D. Rooting habit: Dense.

Plant description:

*Plant type.*—Herbaceous perennial; suitable as a potted plant in containers 15-cm to 25-cm and suitable as a landscape plant in shaded areas.

*Plant and growth habit.*—Short in height and somewhat mounded plant habit; moderately vigorous growth habit and moderate growth rate; potted plants in finished or saleable form in about ten weeks after planting tubers; leaf petioles and leaves arise from one or more growing points on tubers; petioles mostly upright and outwardly arching with development; inflorescences held above the foliar plane on strong upright scapes.

*Plant height, from soil level to top of foliar plane, shadehouse-grown potted plants*.—About 22 cm to 27 cm.

*Plant height, from soil level to top of inflorescences, shadehouse-grown potted plants*.—About 30.5 cm.

*Plant diameter or spread, shadehouse-grown potted plants*.—About 38 cm.

*Number of shoots per plant, shadehouse-grown potted plants, tubers not de-eyed*.—About one to three develop per #1 tuber.

*Number of shoots per plant, shadehouse-grown potted plants, tubers de-eyed*.—About three to four develop per #1 tuber.

*Cataphylls, shadehouse-grown potted plants*.—Length: About 2.8 cm to 7.1 cm. Width: About 1.5 cm. Shape: Wedge-shaped or elongated elliptic. Apex: Acute. Base: Sheathing the stem. Color, inner surface: Close to N155C, occasionally tinged with close to 49D; colors and patterns on the outer surface are visible on the inner surface. Color, outer surface: Close to N170D tinged with close to 182D, streaked, stippled and variably mottled with close to 200B; with development, color becoming closer to 199C and close to 159C stained with close to 187B.

Leaf description:

*Arrangement and type*.—Alternate; simple; fancy-type.

*Length, shadehouse-grown potted plants*.—About 16 cm to 24.8 cm.

*Width, shadehouse-grown potted plants*.—About 10 cm to 14.5 cm.

*Blade aspect*.—Mostly flat or somewhat cupped in the center.

*Shape*.—Ovate.

*Apex*.—Acute to acuminate.

*Base*.—Sagittate to peltate.

*Margin*.—Entire; flat to somewhat wavy with broad undulations.

*Texture, upper and lower surfaces*.—Smooth, glabrous; rigid.

*Luster, upper surface*.—Dull sheen.

*Luster, lower surface*.—Glaucous, dull sheen.

*Venation pattern*.—Pinnate.

*Color, shadehouse-grown potted plants*.—Developing and fully expanded leaves, upper surface: Background color: Close to darker than 147A flushed to deeply flushed with close to 183A to 183B. Margins: Close to 182A; at the edge, close to 183A. Basal notch: Close to 184B. Midvein and primary venation: Close to 50B streaked and tinged with close to 182A and 185A. Areas surrounding venation: Suffused with close to 191A, 191B, 183A, 183B and 184B. Developing and fully expanded leaves, lower surface: Background color: Close to 189A tinged with close to N189A. Margins: Close to 183A. Basal notch: Close to 184B. Midvein: Close to 155C with variable flecks or streaks, close to 184B. Primary venation: Close to 194B with variable flecks or streaks, close to 184B. Lateral venation: Tinged with close to 187A. Areas surrounding venation: Close to N155C with variable flecks and tinged with close to 184B; towards the center of the leaf and along the veins, faintly tinged with close to 187A.

*Petioles*.—Aspect: Initially upright and straight; with development, somewhat outwardly arching. Length, shadehouse-grown potted plants: About 17 cm to 23 cm. Diameter, distally, shadehouse-grown potted plants: About 4 mm to 6 mm. Diameter, proximally, shadehouse-grown potted plants: About 8 mm. Texture: Smooth, glabrous. Luster: Glaucous; proximally, somewhat glossy. Color, shadehouse-grown potted plants: Close to N170D or 182D, stippled, streaked and striped with close to 200B tinged with close to 183B; below the leaf and petiole junction, close to 49D or close to 49D tinged with close to 145D, variably and faintly stippled, streaked and tessellated with close to 200B tinged with close to 183D. Wing length, shadehouse-grown potted plants: About 3.4 cm to 4.5 cm. Wing diameter, shadehouse-grown potted plants: About 8 mm. Texture, inner and outer surfaces: Smooth, glabrous. Luster, inner and outer surfaces: Slightly glossy. Wing color, shadehouse-grown potted plants: Inner surface: Close to N155C variably tinged with close to 49D; occasionally flecked and speckled with close to 183B; colors and patterns on the outer surface are visible on the inner surface. Outer surface: Close to 194D and 147C stippled, streaked and variably mottled with close to 200B, and close to 200B tinged with close to 183D.

Inflorescence description: Inflorescences observed on ten week-old shadehouse-grown potted plants.

*Inflorescence arrangement*.—Upright hooded spathes surrounding a columnar spadix borne on a tall upright scape; spadix with sessile, simple female and male flowers separated into two zones; female flowers develop on the proximal one-third of the spadix; male flowers develop on the distal two-thirds of the spadix; sterile flowers develop at junction of female and male flower zones; near this junction, the spathe constricts and surrounds and encloses the female flowers; spathe open and cupped around male flowers.

*Fragrance*.—Night-fragrant; sweet, jasmine-like with camphor note.

*Natural flowering season and flower longevity*.—Plants of the new *Caladium* typically flower during the spring and summer in central Florida; flowers develop about ten weeks after growth commences; inflorescences last about three days before fading; inflorescences persistent.

*Spathe*.—Length, overall: About 10.8 cm. Length, distal open portion: About 6.8 cm. Length, proximal closed portion: About 4 cm. Width, distal open portion: About 3.8 cm. Depth, distal open portion: About 1.8 cm. Width, at constriction: About 1.3 cm. Width, proximal closed portion: About 2.1 cm. Shape: Elliptic to slightly obovate. Apex: Acuminate. Base: Obtuse. Margin: Entire; flat to slightly recurved. Texture, front and rear surfaces: Smooth, glabrous. Luster, front surface: Glaucous; dull sheen. Luster, rear surface: Slightly glaucous, dull sheen. Color, front surface: Distal open portion: Close to 155C tinged with close to 145D; margins tinged with close to 145C; with development, color becoming closer to 200B to 200C and 199A. Proximal closed portion: Close to 138B to 138C mottled and flushed with close to N186D and 187A; color does not change with development. Color, rear surface: Distal open portion: Close to 155C and 155D with some areas, close to 145C and 145D; color does not change with development. Proximal closed portion: Close to 145C and 145D variably streaked and suffused with close to 194B, 194C and 146D; margin, tinged with close to 54C and 182D; color does not change with development.

*Spadix*.—Length, overall: About 7.6 cm. Length, male flower zone: About 4.4 cm. Length, sterile zone: About 1.6 cm. Length, female flower zone: About 1.6 cm. Diameter, male flower zone: About 9 mm. Diameter, sterile flower zone: About 7.5 mm. Diameter, female flower zone: About 9 mm. Shape: Columnar, spindle-shaped. Apex: Acute. Base: Obtuse. Aspect: Upright. Color, mature, male zone: Close to 158D and 155D. Color, mature, sterile zone: Close to 155D. Color, mature, female zone: Close to 11D. Male flowers: Quantity per spadix: About 150. Shape: Obovate. Height: About 3 mm. Diameter: About 3 mm. Pollen amount: Scarce. Pollen color: Close to 4C. Female flowers: Quantity per spadix: About 60. Shape: Ovate. Height: About 2.5 mm. Diameter: About 2.5 mm. Stigma color: Close to 11D. Ovary color: Close to 11D.

*Scape*.—Length: About 19.7 cm. Diameter: About 6.5 mm. Strength: Sturdy; flexible. Aspect: Mostly erect. Texture: Smooth, glabrous. Luster: Slightly glaucous; dull sheen to slightly glossy. Color: Close to 147D and 145D; proximally, fainted tinged, streaked and stippled with close to 199A to 199B; distally, close to 147D tinged with close to 145C.

*Seeds and fruits*.—To date, seed and fruit development have not been observed on plants of the new *Caladium*.

Disease & pest tolerance: Plants of the new *Caladium* have been observed to have average tolerance to *Xanthomonas* Leaf Spot and *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11. In cooler zones, tubers can be "lifted" prior to first freeze and stored in a cool dry environment overwinter for re-planting the following spring.

It is claimed:

1. A new and distinct *Caladium* plant named 'Berries N' Burgundy' as illustrated and described.

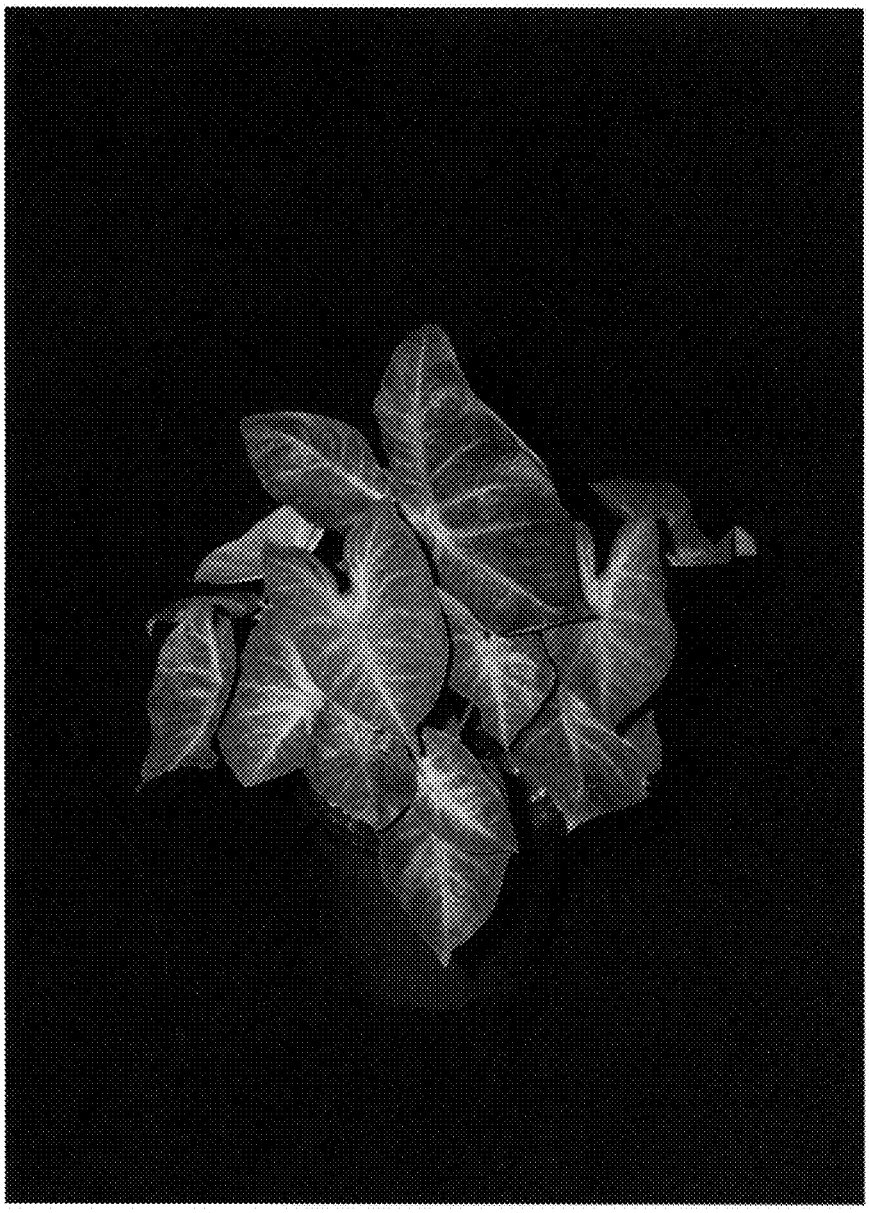

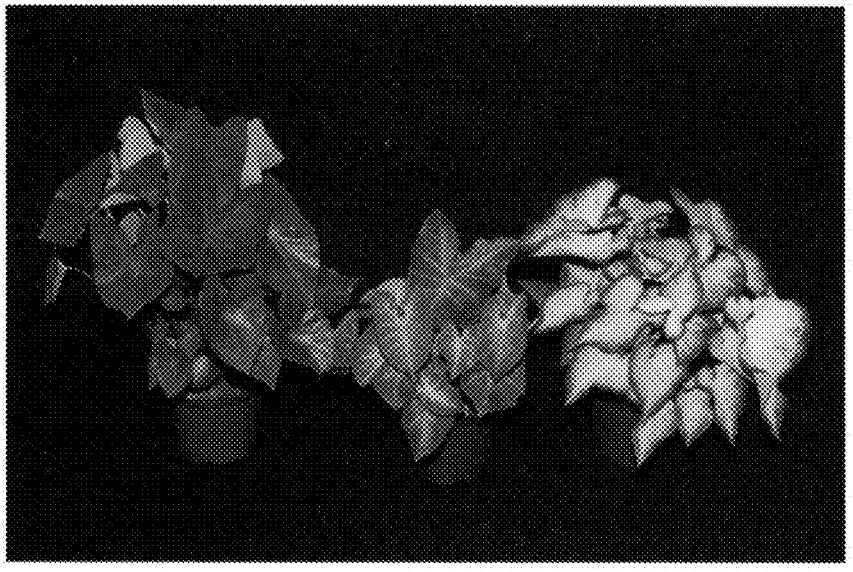
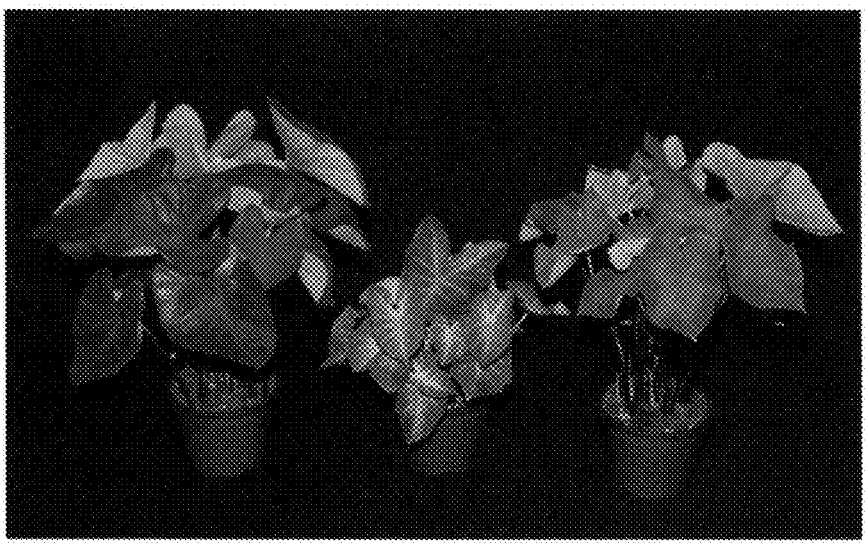

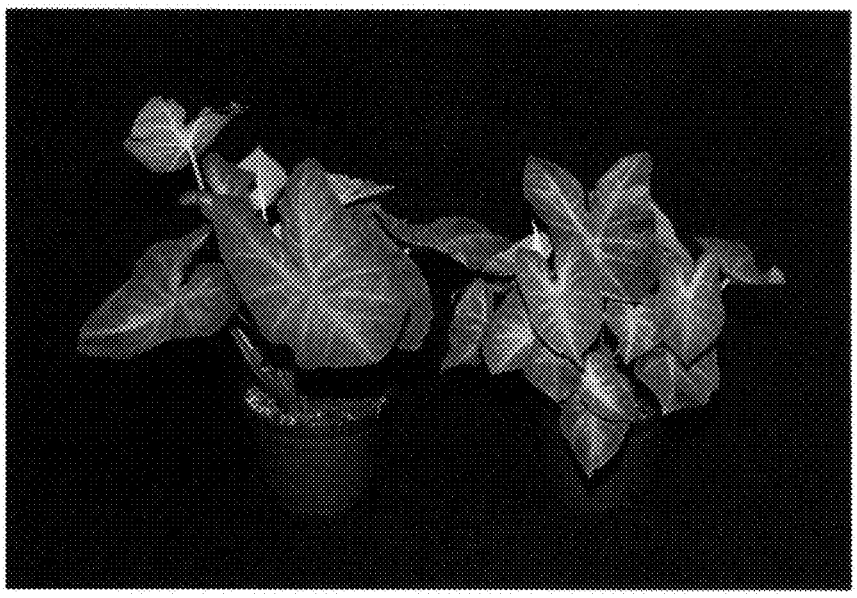
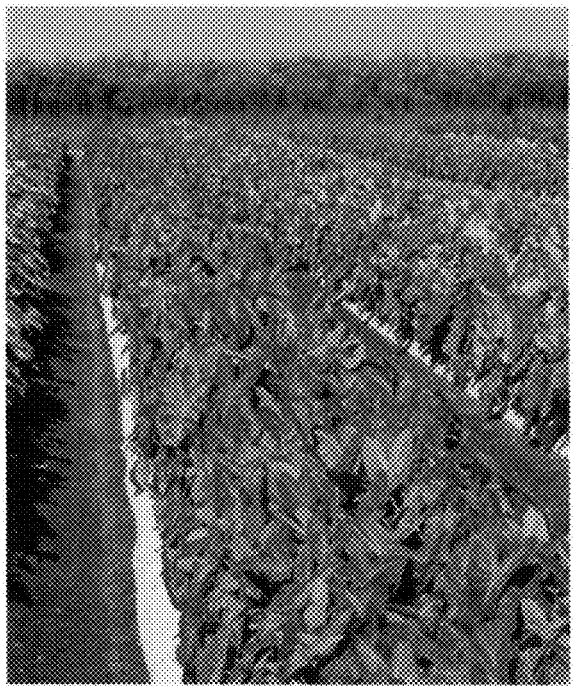

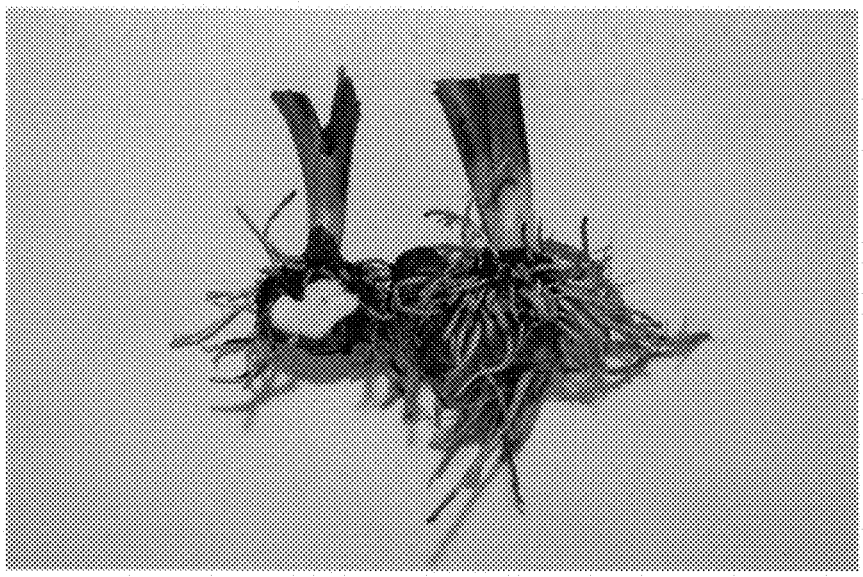
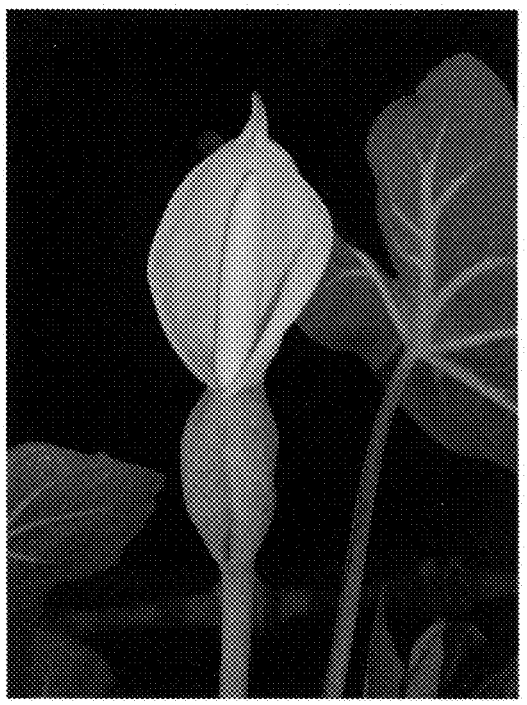

* * * * *